United States Patent [19]

Hoelderich et al.

[11] Patent Number: 5,012,005
[45] Date of Patent: Apr. 30, 1991

[54] CONVERSION OF 1,3-DIOXANES TO 4-OXAALDEHYDES

[76] Inventors: Wolfgang Hoelderich, 18c Mannheimer Strasse; Franz Merger, 25 Max-Slevogt-Strasse, both of 6710 Frankenthal, Fed. Rep. of Germany

[21] Appl. No.: 385,925

[22] Filed: Jul. 27, 1989

Related U.S. Application Data

[63] Continuation of Ser. No. 188,229, Apr. 29, 1988, abandoned.

[30] Foreign Application Priority Data

May 12, 1987 [DE] Fed. Rep. of Germany ....... 3715755

[51] Int. Cl.$^5$ ................... C07C 45/00; C07D 335/00; C07D 307/02
[52] U.S. Cl. .................... 568/427; 568/443; 568/450; 549/13; 549/498
[58] Field of Search ................ 568/427, 443, 450; 549/13, 498

[56] References Cited

U.S. PATENT DOCUMENTS 3,676,500  7/1972  Mantell et al.
4,324,921  4/1982  Arpe.

FOREIGN PATENT DOCUMENTS 2922098  2/1980  Fed. Rep. of Germany.

OTHER PUBLICATIONS

The Journal of the American Chemical Society, vol. 82 (1960) p. 6419.
The Journal of the American Chemical Society, vol. 84 (1962) p. 3307.

*Primary Examiner*—Alan Siegel
*Attorney, Agent, or Firm*—Keil & Weinkauf

[57] ABSTRACT

4-oxaaldehydes of the formula

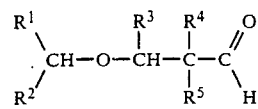

are prepared by catalytic isomerization of 1,3-dioxanes by a process in which a 1,3-dioxane of the formula

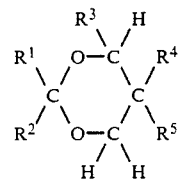

where $R^1$, $R^2$, $R^4$ and $R^5$ are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl, aralkenyl or alkenylaryl radical of 5 to 16 carbon atoms or a heterocyclic radical and furthermore $R^1$ and $R^2$ and/or $R^4$ and $R^5$ together with the carbon atoms to which they are bonded may form a cycloalkane, a cycloalkene or a heterocyclic structure, and the stated radicals may furthermore carry substituents which are inert under the reaction conditions, and $R^3$ is hydrogen or straight-chain or branched alkyl, is isomerized using a metal oxide catalyst, which has been treated with an acid, and/or a silica phase having a zeolite structure.

11 Claims, No Drawings

CONVERSION OF 1,3-DIOXANES TO 4-OXAALDEHYDES

This application is a continuation of application Ser. No. 188,229, filed on Apr. 29, 1988, now abandoned.

The present invention relates to a process for the preparation of 4-oxaaldehydes by catalytic isomerization of 1,3-dioxanes.

It is known that 1,3-dioxane and its derivatives can be subjected to a rearrangement reaction to give β-alkoxyaldehydes (J. Amer. Chem. Soc. 82 (1960), 6419 and J. Amer. Chem. Soc. 84 (1962), 3307). Silica gel and pumice are used as catalysts in this reaction. The catalysts used show pronounced signs of deactivation. Furthermore, their activity and selectivity are not satisfactory from an economic point of view. Owing to the insufficient specificity of the natural product pumice, which may have different compositions depending on its origin, uncontrollable effects on the reaction cannot be avoided (Houben-Weyl, Methoden d. org. Chemie IV, 2, page 149 (1955)).

German Laid-Open Application DOS No. 2,922,698 describes a process for the preparation of β-alkoxypivalaldehydes from 1,3-dioxanes using silica, doped with hydroxide of group III A and/or III B and alkali metal hydroxide, as a catalyst. These catalysts, which constitute only a slight advance in the art, differ from those described previously by virtue of the neutralization of the acid centers. The compounds of the pure lanthanides praseodymium and neodymium, which are required for producing the catalyst, are expensive and are not readily available chemicals. The preferably used commercial lanthanide mixture didymium varies in its composition, so that the industrial catalysts are difficult to reproduce. The catalyst lives stated are only of the order of hours, and no information is given concerning the regeneration of the catalysts.

It is an object of the present invention to provide a process for the preparation of 4-oxaaldehydes from the corresponding 1,3-dioxanes in the presence of a catalyst which is distinguished by being readily and economically available, having high activity and being easy to regenerate. Furthermore, long catalyst lives in combination with high conversions and selectivities should be ensured.

We have found that this object is achieved by a process for the preparation of 4-oxaaldehydes of the formula (I)

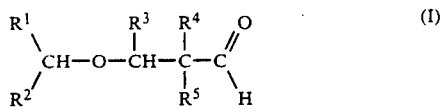

by catalytic isomerization of 1,3-dioxanes, wherein a 1,3-dioxane of the formula (II)

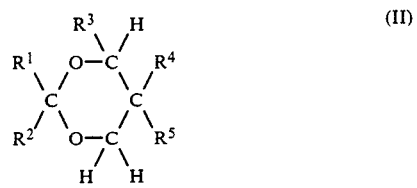

where $R^1$, $R^2$, $R^4$ and $R^5$ in the formulae (I) and (II) are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl, aralkenyl or alkenylaryl radical of 5 to 16 carbon atoms or a heterocyclic radical and moreover $R^1$ and $R^2$ and/or $R^4$ and $R^5$ together with the carbon atom to which they are bonded may form a cycloalkane, cycloalkene or a heterocyclic structure having 5 to 7 ring members, and the stated radicals may furthermore carry substituents which are inert under the reaction conditions, and $R^3$ is hydrogen or straight-chain or branched alkyl, is isomerized using a metal oxide catalyst, which has been treated with an acid, and/or a silica phase having a zeolite structure.

In the novel process, the catalyst requirements stated at the beginning are substantially fulfilled. In view of the prior art, the result of the process is particularly surprising since the said prior art points in the opposite direction, i.e., indicates the exclusion of acid centers. It was therefore not to be expected that excellent results would be obtained within wide limits precisely with acidic metal oxide catalysts which are distinguished by high acidity and, in the case of the silica phases having a zeolite structure, by stringent structural parameters.

The conversion of the 1,3-dioxanes to 4-oxaaldehydes is a good method for preparing, for example, the ethers of the hydroxyneoalkanals in high selectivity and with high conversion, the said ethers being impossible or difficult to obtain by conventional etherification methods.

The conversion may be represented by the following equation:

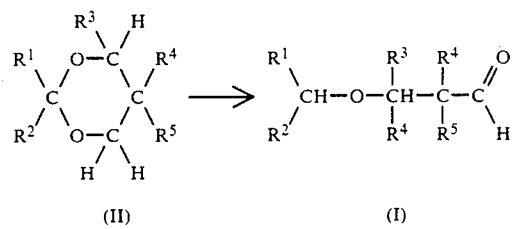

The 1,3-dioxanes of the formula (II) which are used as starting materials, and accordingly the corresponding 4-oxaaldehydes of the formula (I), contain the radicals $R^1$, $R^2$, $R^4$ and $R^5$ which are identical or different and independently of one another are each hydrogen, a straight-chain or branched alkyl, alkenyl or alkynyl radical of not more than 18, in particular 1 to 12, preferably 1 to 6, carbon atoms, a cycloalkyl or cycloalkenyl radical of to 8, in particular 5 or 6, carbon atoms, an aryl, alkylaryl, aralkenyl or alkenylaryl radical of 6 to 16, in particular 6 to 12, carbon atoms, an aromatic saturated or unsaturated heterocyclic structure which contains one or more heteroatoms, such as nitrogen, oxygen or sulfur. The stated radicals may furthermore carry substituents which are inert under the reaction conditions.

The products (I) formed from compound (II) can in turn be further reacted with a diol to give, via an acetal of the general formula (IV)

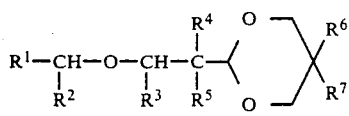

where $R^8$ and $R^7$ have the above definitions of $R^4$ and $R^5$, aldehydes of the structure (formula III)

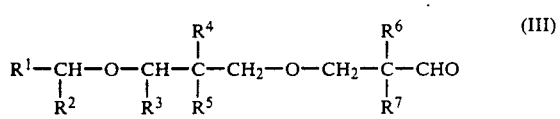

$R^1$ and $R^2$ and/or $R^4$ and $R^5$ and/or $R^6$ and $R^7$, together with the carbon atom to which they are bonded, may furthermore form a cycloalkane, cycloalkene or heterocyclic structure. Suitable radicals $R^3$, regardless of the other radicals, are hydrogen and straight-chain or branched alkyl of 1 to 12, in particular 1 to 8, preferably 1 to 4, carbon atoms.

Alkyl, alkenyl or alkynyl radicals are, for example, methyl, ethyl, n-propyl, isopropyl, propenyl, isopropenyl, n-butyl, isobutyl, n-butenyl, isobutenyl, pentyl, pentenyl, pentynyl, hexyl, hexenyl, heptyl, heptenyl, octyl, octenyl, nonyl, nonenyl, decyl, decenyl, dodecyl and dodecenyl. The alkyl, alkenyl or alkynyl radicals may furthermore carry substituents which are inert under the reaction conditions, for example halogen, alkoxy or carboxyl.

Examples of cycloalkyl radicals are cyclopentyl, cyclohexyl, cycloheptyl, cyclopentenyl and cyclohexenyl.

Examples of suitable aromatic radicals are phenyl, benzyl, 2-phenylethyl, 3-phenylpropyl, 2-phenylpropyl, 4-phenylbutyl, 3-phenylbutyl, 2-phenylbutyl and 3-phenylbutenyl, and these radicals may furthermore be substituted by radicals which are inert under the reaction conditions.

Examples of heterocyclic and heteroaromatic radicals are tetrahydrofuran, dihydrofuran, furan, tetrahydrothiophene (thiophane), dihydrothiophene, thiophene, pyridine and thiopyran radicals. These radicals may furthermore be substituted by radicals which are inert under the reaction conditions, such as alkyl or halogen.

Starting materials which are particularly suitable for the novel process are 1,3-dioxanes in which $R^3$ is hydrogen while $R^4$ and $R^5$ are each one of the stated organic radicals.

The starting compounds of the formula (II) can be prepared by a conventional method from aldehydes or ketones or their readily cleavable derivatives, for example dialkyl ketals or acetals, and 1,3-diols in accordance with the following equation:

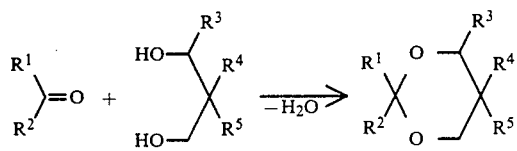

Examples of suitable diol components are the following compounds: propane-1,3-diol, 2-methyl-, 2-ethyl-, 2-phenyl-, 2,2-dimethyl-, 2,2-diethyl-, 2-methyl-2-ethyl-, 2-methyl-2-propyl, 2-methyl-2-butyl-, 2-methyl-2-phenyl- and 2-ethyl-2-butylpropane-1,3-diol, 1,1-dimethylolcyclohexane and -pentane, 3,3-dimethyloltetrahydrofuran and -pyran and 2,2,4-trimethylpentane-1,3-diol.

Examples of suitable carbonyl components are aliphatic, aromatic or heterocyclic aldehydes and ketones and their acetals and ketals with low-boiling alcohols.

Examples of saturated aliphatic aldehydes are formaldehyde, acetaldehyde, propionaldehyde, butyraldehyde, pentanal, hexanal and higher homologous n-alkanals, such as decanal, isobutyraldehyde, 2-methylbutanal, 3-methylbutanal, 3,3-dimethylbutanal, 2-methylpentanal, 2-ethylhexanal and 2-methyldecanal, glyoxal, methylglyoxal, malondialdehyde, succindialdehyde and glutardialdehyde.

Examples of heterocyclic aldehydes are tetrahydrofuran-2-aldehyde and -3-aldehyde, tetrahydrothiophene-2- and -3-aldehyde, 5,6-dihydropyran-6-aldehyde, 2,5-dimethyl-2,6-dihydropyran-6-aldehyde, furan-2-aldehyde and -3-aldehyde, thiophene-3-aldehyde and pyridine-2-, -3- and -4-aldehyde.

Examples of suitable ketones are the following compounds: acetone, methyl ethyl ketone, diethyl ketone, methyl isopropyl ketone, diisopropyl ketone, diisobutyl ketone, methyl isobutyl ketone, methoxyacetone, methyl vinyl ketone, methyl isopropenyl ketone, methyl isobutenyl ketone, cyclopentanone, cyclohexanone, methylcyclopentanones, methylcyclohexanones, cyclohexenone, 3,5,5-trimethylcyclohexen-2-one, methyl, ethyl and vinyl phenyl ketone, methyl furyl ketone, acetylacetone and ethyl acetoacetate.

Examples of other substituted alkanals are 3-hydroxy-2,2-dimethylpropanal, methoxy- and butyoxypivalaldehyde, 4-acetoxybutyraldehyde and ethyl 5-formylvalerate.

It is also possible to use unsaturated aldehydes, for example acrolein, α-methylacrolein, α-ethylacrolein and higher α-alkyl-, isoalkyl- and alkenylacroleins, such as but-2-enal, 2-methyl-but-2-enal, 2-methylpent2-enal, 2-ethylhex-2-enal, 2,2-dimethylpent-4-enal, 2-methyl-4-acetoxybut-2-enal, 2-methoxymethylacrolein, 2-(3-methoxycarbonylpropyl)-acrolein or 2-methyl-4-chlorobut-2-enal.

Examples of aromatic aldehydes are benzaldehyde, p-methoxybenzaldehyde, phenylacetaldehyde, 2-phenyl- and 3-phenylpropanal, 2-hydroxybenzaldehyde, 3-hydroxy-4-methoxybenzaldehyde, cinnamaldehyde and benzylacrolein.

Metal oxide catalysts, which have been treated with an acid, and/or silica phases having a zeolite structure are used as catalysts for the novel conversion of 1,3-dioxanes.

Examples of suitable metal oxide catalysts are the acidic oxides of elements of main group III and IV and subgroups IV to VI of the Periodic Table, in particular oxides such as silicon dioxide in the form of silica gel, kieselguhr or quartz, as well as titanium dioxide, zirconium dioxide, phosphorus oxides, vanadium pentoxide, niobium oxide, boron trioxide, alumina, chromium oxides, molybdenum oxides, tungsten oxides, iron oxides and mixtures of these oxides.

Examples of suitable inorganic acids are HF, HCl, HBr, HI, $H_2SO_4$, $H_2SO_3$, $HNO_3$, $H_3BO_3$, phosphoric acids and mixtures of these.

For example, formic acid, acetic acid, propionic acid and oxalic acid and mixtures of these may be used as organic acids. Mixtures of inorganic and organic acids may also be employed.

The treatment of the metal oxides, for example of the SiO₂ (silica), with acids can be carried out both on the molded and on the unmolded material. In an advantageous procedure, for example, SiO₂ in powder form is treated with 1 N acid for 1 hour at 80° C. After the treatment, the product is washed with water, dried at 110° C. for 16 hours and calcined at 500° C. for 20 hours. In another procedure, for example, SiO₂ is treated, before or after it has been molded, with a 3–25, in particular 12–20, % strength by weight aqueous hydrochloric acid for from 1 to 3 hours at from 60° to 80° C. Thereafter, the SiO₂ treated in this manner is washed with water, dried, and calcined at from 400° to 500° C.

In a particular embodiment of the acid treatment, the SiO₂ is treated, before it has been molded, with hydrofluoric acid, in general 0.001–2N, preferably 0.05–0.5N, hydrofluoric acid, at elevated temperatures, for example by refluxing in general for from 0.5 to 5, preferably from 1 to 3, hours. After isolation, for example by filtering off and washing the material thoroughly, the latter is advantageously dried at from 100° to 160° C. and calcined at from 450° to 600° C. In another preferred embodiment of the acid treatment, the SiO₂ is treated, after it has been molded, with from 12 to 20% strength by weight hydrochloric acid at elevated temperatures, for example from 50° to 90° C., preferably from 60° to 80° C., for from 0.5 to 5, preferably from 1 to 3, hours. This material is then washed thoroughly, dried at from 100° to 160° C. and calcined at from 450° to 600° C. An HF treatment may also be followed by an HCl treatment.

Catalysts treated with phosphoric acids may also be used. Phosphoric acid is applied to, for example, SiO₂, Al₂O₃ or TiO₂ carriers by impregnation or spraying. A catalyst containing phosphoric acid can be obtained, for example, by treating H₂PO₄ or NaH₂PO₄ solution on SiO₂ and then carrying out drying and calcination. However, phosphoric acid can also be sprayed together with silica gel into a spray tower. This is followed by drying and in general calcination. Phosphoric acid can also be sprayed onto the carrier in an impregnating mill.

Other catalysts which are suitable for the novel conversion are the Silicalites ® or molecular sieves, ie. silica polymorphs. Silicalites can be prepared, for example, from silica sols in the presence of tetrapropylammoniumhydroxide and, if required, an alkali metal hydroxide under hydrothermal conditions at from 150° to 250° C. The Silicalite powders prepared in this manner can be isolated, dried at from 100° to 160° C., preferably 110° C., and calcined at from 350° to 500° C., preferably from 450° to 500° C., and then molded with a binder in a weight ratio of from 90:10 to 20:80 to give extrudates or pellets. Suitable binders are various aluminas, preferably boehmite, amorphous aluminosilicates having an SiO₂/Al₂O₃ ratio of from 25:75 to 90:5, preferably 75:25, silica, preferably finely divided SiO₂, mixtures of finely divided SiO₂ and finely divided Al₂O₃, TiO₂, ZrO₂ and clay. After they have been molded, the extrudates or pellets are dried at 110° C. for 16 hours and calcined at 500° C. for 16 hours.

Advantageous catalysts are also obtained if the Silicalite isolated is molded directly after drying and is not subjected to calcination until after the molding procedure. The Silicalite powders prepared can also be used in pure form, without a binder, as extrudates or pellets, the extrusion or peptizing assistants used being, for example, ethylcellulose, stearic acid, potato starch, formic acid, oxalic acid, acetic acid, nitric acid, ammonia, amines, silicoesters or graphite or a mixture of these. The Silicalites can be subjected to the same modifications as described above in order to achieve very high selectivity, high conversion and long catalyst lives.

It is also often advantageous to treat the silicates with ammonium ions and then to carry out drying, and calcination at from 350° to 550° C., preferably from 450° to 500° C.

Other processes for the preparation of silicates are described in U.S. Pat. No. 4,061,724 and German Laid-Open Application DOS No. 2,743,143.

These Silicalites can likewise be treated with acids as described above in order to improve the selectivity, conversion and catalyst life.

In order to achieve high selectivity, high conversion and long catalyst lives with the Silicalites, it may be advantageous to modify them. In a suitable method of modifying the catalysts, for example, the unmolded or molded Silicalites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Ni, transition metals of subgroups 4–8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, and rare earth metals, such as La, Ce, Pr, Nd, Er, Yb and U.

In a possible embodiment, for example, Cu(NO₃)₂ · 3H₂O or Ni(NO₃)₂ · 6H₂O or Ce(NO₃)₃ · 6H₂O or La(NO₃)₂ · 6H₂O or Cs₂CO₃ is dissolved in water and this solution is used to impregnate the molded or unmolded Silicalite for a certain time, ie. about 30 minutes. Any supernatant solution is freed from water in a rotary evaporator. Thereafter, the impregnated Silicalite is dried at about 150° C. and calcined at about 550° C. This impregnation process can be carried out several times in succession in order to obtain the desired metal content.

It is also possible to prepare an aqueous Ni(NO₃)₂ solution or ammoniacal Pd(NO₃)₂ solution and to suspend the pure Silicalite powder therein at from 40° to 100° C. for about 24 hours, while stirring. After the product has been filtered off, dried at about 150° C. and calcined at about 500° C., the material thus obtained can be further processed with or without a binder to give extrudates, pellets or fluidizable material.

The H form or ammonium form or alkali metal form of the Silicalites present can be subjected to ion exchange by taking this material in the form of extrudates or pellets in a column and circulating an aqueous Ni(NO₃)₂ solution or ammoniacal Pd(NO₃)₂ solution over the said Silicalite at slightly elevated temperatures of from 30° to 80° C. for from 15 to 20 hours. The product is then washed thoroughly with water and calcined at about 550° C.

In the case of some metal-doped Silicalites, e.g. Pd-, Cu- and Ni-doped Silicalites, aftertreatment with water is advantageous.

By precoking, it is possible to adjust the activity of the catalyst to obtain optimum selectivity with respect to the desired reaction product.

The catalysts described here can alternatively be used in the form of 2–4 mm extrudates, pellets of 3–5 mm diameter or powders having particle sizes of from 0.1 to 0.5 mm or as a fluidized catalyst.

The reaction conditions selected for the novel conversion in the gas phase, which is preferred, are from 200° to 500° C., preferably from 230° to 400° C., and a WHSV of from 0.1 to 20 h⁻¹, preferably from 0.5 to 5 h$^{-1}$ (g of 1,3-dioxane per g of catalyst per hour). The reaction can be carried out in a fixed bed or fluidized bed. It is also possible to effect the reaction in the liquid phase by the suspension, trickle-bed or liquid phase method at from 50° to 200° C. In general, the conversion increases sharply with increasing temperature, whereas the selectivity decreases only slightly within a certain temperature range.

The process can be carried out under atmospheric pressure or, depending on the volatility of the starting compound, under reduced or superatmospheric pressure; a continuous procedure is preferred.

Sparingly volatile or solid starting materials can be used in dissolved form, for example in solution in tetrahydrofuran, toluene or petroleum ether. The starting material may furthermore be diluted with such solvents or with inert gases, such as $N_2$, Ar or steam.

After the reaction, the corresponding 4-oxaaldehydes are isolated from the reaction mixture by a conventional method, for example by distillation; unconverted 1,3-dioxanes (II) are, if desired, recycled to the novel reaction.

The compounds obtainable by the novel process and a number of their derivatives are of interest as biologically active compounds, for example as bactericides, and are also useful intermediates. They can be further processed by a conventional method and in a simple manner to give amines, alcohols and acids, for example by oxidation with oxygen or by reduction, eg. by catalytic hydrogenation or hydrogenation under aminating conditions.

The novel compound of the formula

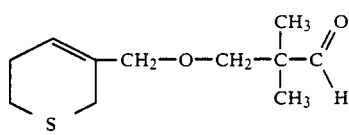

has a melting point of 53.8° C. and a boiling point of 121°–125° C.

EXAMPLES 1 TO 34

The reactions are carried out under isothermal conditions in a tubular reactor (coil, 0.6 cm internal diameter, 90 cm length) in the gas phase for not less than 6 hours. Separation and characterization of the reaction products are effected by conventional methods. The reaction products (I) and the starting materials (II) are quantitatively determined by gas chromatography.

The catalysts used in the Examples for the conversion of 1,3-dioxanes to 4-oxaaldehydes are:

Catalyst A 100 g of $SiO_2$ extrudates (D 11-10 ®) are treated with 600 ml of 15% strength HCl at 80° C. for 1 hour. Thereafter, the material is washed Cl-free, dried at 110° C. and calcined at 600° C. for 1 hour.

Catalyst B 100 g of $SiO_2$ extrudates (D 11-10) are refluxed with 280 ml of 0.1N HF and 80 ml of $H_2O$ for 1 hour. Thereafter, the material is washed neutral, dried at 110° C. and calcined at 500° C. for 5 hours.

Catalyst C 50 g of catalyst B are treated in 300 ml of 15% strength HCl at 80° C. for 1 hour. Thereafter, the material is washed Cl-free, dried at 100° C. and calcined at 600° C. for 1 hour.

Catalyst D 660 g of silica sol (30% by weight of $SiO_2$) are mixed with 567 g of 20% strength aqueous tetrapropylammoniumhydroxide solution and reacted in an autoclave at 200° C. for 72 hours. After removal of the mother liquor, the product is dried at 120° C. and calcined at 500° C. for 16 hours. The X-ray diffraction pattern typical of the Silicalites is obtained. This powder is molded with a molding assistant to give 2 mm extrudates, which are dried at 110° C. and calcined at 500° C. for 16 hours.

Catalyst E

Catalyst E is obtained by subjecting catalyst D to ion exchange with a 20% strength $NH_4Cl$ solution at 80° C. until the Na content is 0.015% by weight (after drying at 110° C. and calcination at 500° C. for 5 hours).

Catalyst F $Al_2O_3$ (D 10-10 ®) is impregnated with $H_3BO_3$, dried at 130° C. for 2 hours and calcined at 540° C. for 2 hours. Catalyst F is composed of 85% of $Al_2O_3$ and 15% of $B_2O_3$.

Catalyst G

Catalyst G is obtained by treating D 10-10 ($Al_2O_3$) with 85% strength $H_3PO_4$ for 30 minutes and then drying the product at 130° C. for 2 hours and calcining it at 540° C. for 2 hours. The P content is 4.9% by weight.

Catalyst H

D 11-10 ($SiO_2$) is treated with $H_3BO_3$ in methanolic solution and dried at 110° C. and calcined at 500° C. for 5 hours. The $B_2O_3$ content of catalyst H is 3.0% by weight.

Catalyst I (comparison catalyst) D 11-10 ($SiO_2$).

Catalyst J (comparison catalyst) D 10-10 ($Al_2O_3$).

Catalyst K (comparison catalyst)

$TiO_2$ (P 25 ®) is molded to give 2 mm extrudates, which are dried at 110° C. and calcined at 500° C. for 16 hours.

Catalyst L (comparison catalyst)

Commercial MgO in pellet form.

Catalyst M

Catalyst M is obtained by treating catalyst L as described for catalyst B.

Catalyst O (comparison catalyst)

Catalyst O is prepared according to German Laid-Open Application DOS No. 2,922,698. In this procedure, 51 g of a commercial $SiO_2$ (D 11-11 ®) are impregnated with a solution of 5.1 g of 0.1N $CH_3COOH$, 3.19 g of $Pr(NO_3)_3 \cdot 5H_2O$, 3.21 g of $Nd(NO_3)_3 \cdot 5H_2O$ and 2.66 g of $CH_3COOK$, dried, and calcined at 600° C. for 4 hours.

The experimental results obtained with these catalysts are listed in Tables 1 and 2 below.

TABLE 1

$$R-\underset{O}{\overset{O}{\underset{|}{\bigg\langle}}}\bigg\rangle \quad (II) \longrightarrow R-CH_2-O-\underset{CH_3}{\overset{CH_3}{\underset{|}{C}}}-\overset{O}{\underset{H}{C}} \quad (I)$$

| Example | 1 | 2 | 3 | 4[1] | 5[1] | 6[1] | 7[1] |
|---|---|---|---|---|---|---|---|
| R | | | | $CH_3CH_2CH_2-$ | | | |
| Catalyst | A | F | M | J | K | L | O |
| Temp. °C. | 300 | 300 | 300 | 300 | 300 | 300 | 300 |
| WHSV $h^{-1}$ | 3 | 3 | 3 | 3 | 3 | 3 | 3 |
| Conversion II, % | 74.5 | 53.3 | 23.3 | 22.2 | 5.0 | 5.6 | 28.5 |
| Selectivity I, % | 87.7 | 79.2 | 75.2 | 71.6 | 26.0 | 5 | 13.2 |

Comparative Example 7 shows that the catalyst 0 described in German Laid-Open Application DOS 2,922,698 is effective for only short reaction times of from 1 to 2 hours, the activity decreasing virtually to zero after 4 hours.

| Example | 8 | 9 | 10 | 11 | 12 | 13 | 14 | 15 | 16 |
|---|---|---|---|---|---|---|---|---|---|
| R | $CH_3CH_2CH_2CH_2-\underset{C_2H_5}{\overset{|}{CH}}-$ | | $CH_3CH_2CH_2CH=\underset{C_2H_5}{\overset{|}{C}}-$ | | Ph-CH(Ph)- | $Ph-\underset{CH_3}{\overset{|}{CH}}-$ | $CH_3O-$ | $CH_3O-C_6H_4-$ | |
| Catalyst | A | A | C | E | I[1] | A[2] | E[2] | A | A |
| Temp. °C. | 250 | 300 | 300 | 300 | 300 | 300 | 300 | 300 | 300 |
| WHSV $h^{-1}$ | 2 | 2 | 2 | 2 | 2 | 2 | 2 | 2 | 2 |
| Conversion II, % | 86.9 | 94.6 | 93.1 | 92.8 | 96.6 | 84.3 | 85.0 | 89.3 | 100 |
| Selectivity I, % | 84.8 | 53.8 | 64.3 | 77.7 | 29.2 | 79.5 | 60.0 | 85.8 | 67.9 |

| Example | 17 | 18 | 19 | 20 | 21 |
|---|---|---|---|---|---|
| 15 R | | | $CH_3O-C_6H_4-$ | | |
| Catalyst | E | G | H | F | I[1] |
| Temp. °C. | 300 | 300 | 300 | 300 | 300 |
| WHSV $h^{-1}$ | 2 | 2 | 2 | 3 | 2 |
| Conversion II, % | 48.2 | 39.4 | 95.3 | 40.8 | 72.0 |
| Selectivity I, % | 62.4 | 86.0 | 62.8 | 81.4 | 67.9 |

[1]Comparative Examples
[2]Diluted with tetrahydrofuran; acetal:tetrahydrofuran = 50:50

TABLE 2

| Example | 22 | 23 | 24 | 25 | 26 | 27 | 28 | 29 | 30 |
|---|---|---|---|---|---|---|---|---|---|
| Reaction | A. | A. | B. | B. | B. | B. | C. | C. | D. |
| Catalyst | A | B | A | A | B | C | A | D | A |
| Temp. °C. | 250 | 300 | 250 | 300 | 300 | 300 | 300 | 300 | 300 |
| WHSV $h^{-1}$ | 2 | 2 | 2 | 2 | 2 | 2 | 2.5 | 2 | 2 |
| Conversion II, % | 94.1 | 97.3 | 18.2 | 78.1 | 56.6 | 75.1 | 10.9 | 8.8 | 64.7 |
| Selectivity I, % | 69.9 | 51.8 | 95.6 | 79.5 | 90.6 | 73.5 | 71.6 | 67.0 | 95.0 |

Reactions:

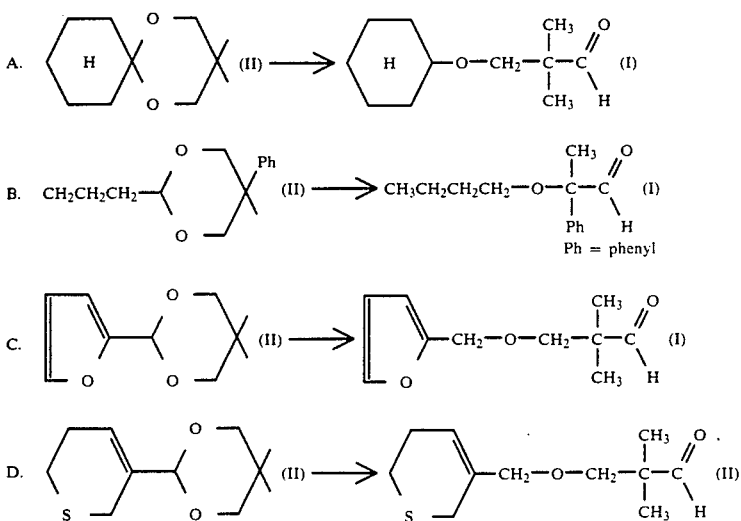

1. (Twice Amended) A process for preparing a 4-oxaaldehyde of the formula (I)

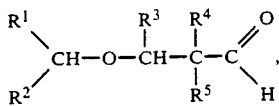

which comprises isomerizing a 1,3-dioxane of the formula (II)

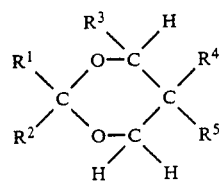

in the presence of an acidic metal oxide catalyst that has been obtained by treatment with an inorganic acid, where $R^1$, $R^2$, $R^4$, and $R^5$ in the formulae (I) and (II) are identical or different and are each hydrogen, a straight-chain or branched alkyl, alkenyl or alkynyl radical of not more than 18 carbon atoms, a cycloalkyl or cycloalkenyl radical of 5 to 8 carbon atoms, an aryl, alkylaryl, aralkyl, aralkenyl or alkenylaryl radical of 5 to 16 carbon atoms or a heterocyclic radical and moreover $R^1$ and $R^2$ and/or $R^4$ and $R^5$ together with the carbon atom to which they are bonded may form a cycloalkane, cycloalkene or a heterocyclic structure, and the stated radicals may furthermore carry substituents which are inert under the reaction conditions, and $R^3$ in the formulae I and II is hydrogen or straight-chain or branched alkyl 2. The process of claim 1, wherein an acetal or ketal of propane-1,3-diol, of 2-methyl-, 2,2-dimethyl-, 2-methyl-2-ethyl-, 2-methyl-2-propyl-, 2-methyl-2-butyl-, 2-methyl-2-phenyl- or 1-isopropyl-2,2-dimethylpropane-1,3-diol or of 1,1-dimethylolcyclohexane or -pentane is isomerized.

3. The process of claim 1, where the catalyst used is an oxide of the elements Si, Al, Ti, Zr or Ce, which has been treated with an acid selected from the group consisting of: HCl, HF, $H_3PO_4$, $H_3BO_3$, and a mixture thereof.

4. The process of claim 9, wherein the catalyst used is a hydrothermally prepared silica phase having a pentasil structure.

5. The process of claim 1, wherein the reaction is carried out in the gas phase.

6. The process of claim 1, wherein the catalyst is $SiO_2$ which has been treated with HCl, HF, $H_3PO_4$, $H_3BO_3$ or a mixture thereof.

7. The process of claim 1, wherein the catalyst is $SiO_2$ which has been treated with HCl.

8. A process for preparing a 4-oxaaldehyde of the formula (I)

9. The process of claim 3, wherein the isomerization is carried out at from 230° to 400° C. and 0.1 to 20 g of 13 dioxane are used per g of catalyst per hour.

10. The process of claim 9, wherein 0.5 to 5 g of 1,3 dioxane are used per g of catalyst per hour.

11. The process of claim 8, wherein the silica phase zeolite is doped with metal salts.

* * * * *

UNITED STATES PATENT AND TRADEMARK OFFICE
CERTIFICATE OF CORRECTION

Page 1 of 3

PATENT NO. : 5,012,005
DATED : April 30, 1991
INVENTOR(S) : Hoelderich, et. al.

It is certified that error appears in the above-indentified patent and that said Letters Patent is hereby corrected as shown below:

In claim 1, column 11, line 1: delete "(Twice Amended)"

In claim 4, column 12, line 16: "The process of claim 9" should read

--The process of claim 1--

In claim 8, column 12, line 28, after "(I)" insert:

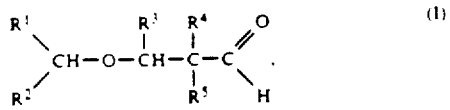

which comprises isomerizing a 1,3-dioxane of the formula (II)

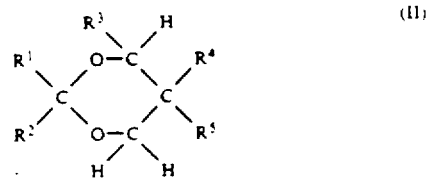

UNITED STATES PATENT AND TRADEMARK OFFICE
CERTIFICATE OF CORRECTION

PATENT NO. : 5,012,005

DATED : Apr. 30, 1991

INVENTOR(S) : HOELDERICH et al.

It is certified that error appears in the above-identified patent and that said Letters Patent is hereby corrected as shown below:

in the presence of a silica phase having a zeolite structure, where $R^1$, $R^2$, $R^4$, and $R^5$ in the formulae (I) and (II) are identical or different and are each hydrogen, a straight-chain or branched alkyl, or alkynyl radical of not more than 18 carbon atoms, a cycloalkyl or cycloalkenyl radical of 5 to 8 carbon atoms, an aryl, alkylaryl, aralkyl, aralkenyl or alkeylaryl radical of 5 to 16 carbon atoms or a heterocyclic radical and where $R^1$ and $R^2$ or $R^4$ and $R^5$ together with the carbon atom to which they are bonded may form a cycloalkane, cycloalkene or a heterocyclic structure, and the stated radicals may furthermore carry substituents which are inert under the reaction conditions, and $R^3$ in the formulae I and II is hydrogen or straight chain or branched alkyl. --

UNITED STATES PATENT AND TRADEMARK OFFICE
CERTIFICATE OF CORRECTION

PATENT NO. : 5,012,005
DATED : April 30, 1991
INVENTOR(S) : Hoelderich, et. al.

It is certified that error appears in the above-indentified patent and that said Letters Patent is hereby corrected as shown below:

Column 12, Claim 9, line 31, "13 dioxane" should read --1,3 dioxane--

Signed and Sealed this

First Day of February, 1994

Attest:

BRUCE LEHMAN

*Attesting Officer*      *Commissioner of Patents and Trademarks*